United States Patent [19]

Nagafuzi et al.

[11] Patent Number: 5,290,569
[45] Date of Patent: Mar. 1, 1994

[54] COATED COMPOSITION AND ITS PREPARATION PROCESS

[75] Inventors: Noboru Nagafuzi, Sakai; Takayuki Tsukada, Itami; Kazuhiro Shima, Toyonaka; Yasushi Takagishi, Ashiya; Yusuke Suzuki, Izumi; Yoshitaka Tomoda; Takashi Hayashi, both of Osaka, all of Japan

[73] Assignee: Shionogi & Co., Ltd., Osaka, Japan

[21] Appl. No.: 895,466

[22] Filed: Jun. 8, 1992

Related U.S. Application Data

[63] Continuation of Ser. No. 684,388, Apr. 12, 1991, abandoned.

[30] Foreign Application Priority Data

Apr. 12, 1990 [JP] Japan .................................. 2-096663

[51] Int. Cl.⁵ ............................................. A61K 9/16
[52] U.S. Cl. ................................ 424/490; 424/497; 424/498
[58] Field of Search ............... 424/489, 490, 493, 498, 424/502

[56] References Cited

U.S. PATENT DOCUMENTS

| | | | |
|---|---|---|---|
| 3,670,065 | 6/1972 | Eriksson et al. | 264/131 |
| 4,146,653 | 3/1979 | Mader et al. | 427/3 |
| 4,450,877 | 5/1989 | Walker et al. | 141/1 |
| 4,894,234 | 1/1990 | Sharma et al. | 424/498 |
| 4,935,246 | 6/1990 | Ahrens | 424/498 |
| 4,948,589 | 8/1990 | Iijima et al. | 424/498 |
| 4,971,804 | 11/1990 | Ghebre-Sellassie | 424/498 |
| 5,206,219 | 4/1993 | Desai | 424/490 |

FOREIGN PATENT DOCUMENTS

| | | |
|---|---|---|
| 0078599 | 5/1983 | European Pat. Off. |
| 0177368 | 4/1986 | European Pat. Off. |
| 0237345 | 9/1987 | European Pat. Off. |
| 0256127 | 2/1988 | European Pat. Off. |
| 0368247 | 5/1990 | European Pat. Off. |
| 3721721 | 6/1988 | Fed. Rep. of Germany |

Primary Examiner—Thurman K. Page
Assistant Examiner—Amy Hulina
Attorney, Agent, or Firm—Wenderoth, Lind & Ponack

[57] ABSTRACT

A process for preparing a coated composition comprising a pharmaceutically active substance stable to heat, which comprises centrifugally granualting a mixture comprising said active substance and a first thermomelting material as a binder under heating without using any solvent and coating the resultant granules with a second thermomelting material as a coating material under heating, the melting point of the second thermomelting material being lower than that of the first thermomelting material.

8 Claims, 3 Drawing Sheets

○  The 1st test solution
●  Purified water

○ The 1st test solution
● Purified water

COATED COMPOSITION AND ITS PREPARATION PROCESS

This application is a continuation of now abandoned application, Ser. No. 07/684,388 filed Apr. 12, 1991.

The present invention relates to a coated composition and its preparation process. More particularly, it relates to an orally administrable coated composition comprising a pharmaceutically active substance stable to heat, and its preparation process.

For preparation of an orally administerable composition comprising a pharmaceutically active substance, there is commonly adopted a wet granulating and/or coating procedure using a solvent such as water or an organic solvent. When said active substance is sensitive to a solvent, however, such wet procedure is not applicable. In this case, the pharmaceutically active substance or its mixture with any additive such as a filler or a diluent is obliged to be supplied in the form of a powdery preparation, or shall be compressed and granulated to make a granular preparation. The powdery or granular preparation is, when desired, filled in gelatin capsules to make a capsule preparation or compressed to make a tablet preparation. Since these preparations are uncoated, they may afford an unpleasant taste to patients who take them. Further, such non-coating makes it difficult to control the site or time at which the pharmaceutically active substance exerts its pharmaceutical efficacy.

In order to make a pharmaceutically active substance sensitive to a solvent coated, an extensive study has been made, and as the result, there is now completed a new process for preparing a coated composition comprising a pharmaceutically active substance without using any solvent.

According to this invention, there is provided a process for preparing a coated composition comprising a pharmaceutically active substance stable to heat, which comprises the steps of granulating a mixture comprising said active substance and a first thermomelting material as a binder under heating without using any solvent and coating the resultant granules with a second thermomelting material under heating.

Figure 1:
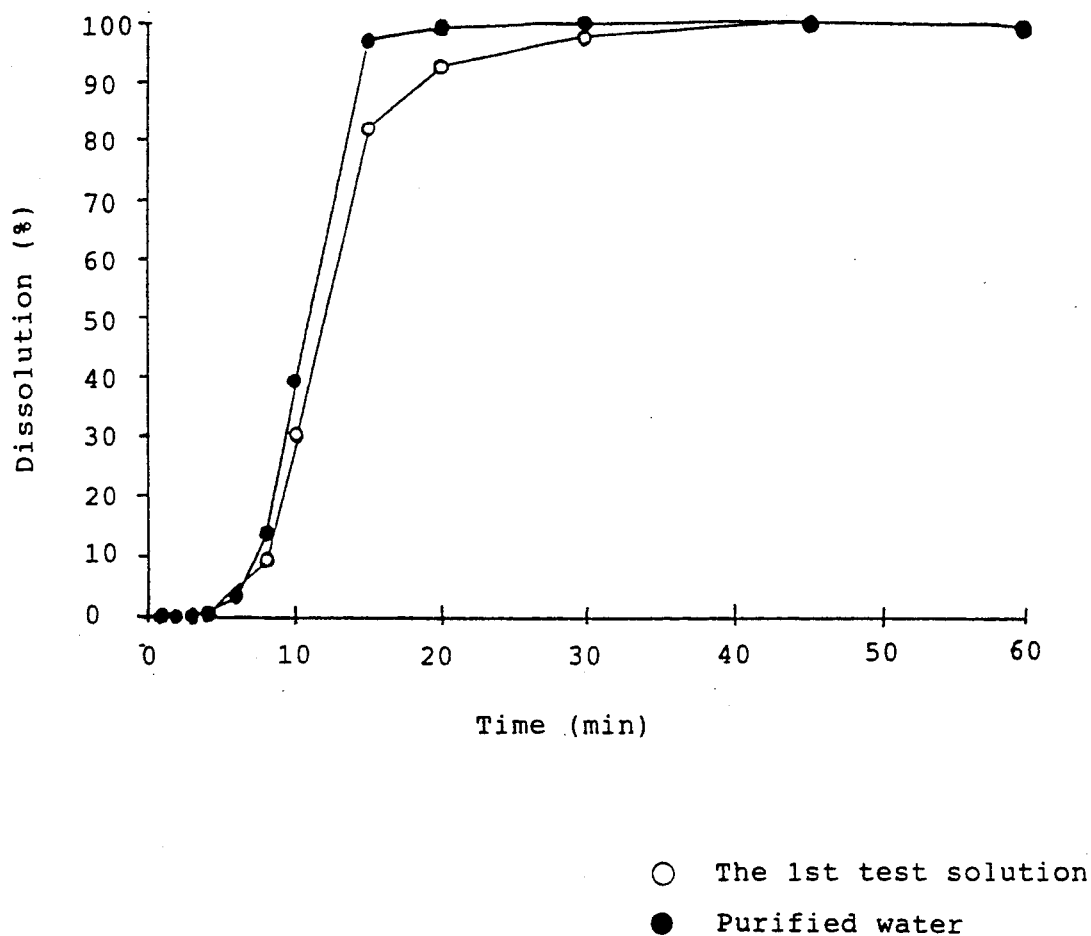
FIGS. 1-3 illustrate the dissolution properties of the coated granules.

In view of the characteristic nature of the process, the pharmaceutically active substance is required to be the one which is stable to heat, for instance, substantially stable at a temperature not exceeding about 200° C. The process is advantageously applicable, particularly when said active substance is sensitive to a solvent such as water or an organic solvent, because the process does not require any solvent. The term "sensitive" herein used means that the pharmaceutically active substance is readily (e.g. within about one hour) influenced by a solvent to such an extent that its physical, chemical and/or biological properties are substantially modified or changed. Specific examples of the pharmaceutically active substances are antihistamines including terfenadine, chlorpheniramine maleate, clemastine fumarate, carbinoxamine maleate, prometahzine hydrochloride, and diphenhydramine salycylate; analgesics and antipyretics including aspirine, salicylamide, ethanzamide, acetaminophen and diclofenac sodium; bronchodilators including S-1452 and cyclophosphamide; antitussives and expectorants including dextromethorphan hydrobromide, dihydrocodeine phosphate, cloperastine hydrochloride, phenylpropanolamine hydrochloride, methylephedrine, potassium cresol sulfonate, morphine sulphate, codeine phosphate and belladonna total alkaloids; antiulcers including benexate hydrochloride betadex (hereinafter referred to as "TA 903"), pirenzepine, cetraxate, ranitidine and famotidine; drugs for circuratory organs including pindolol, propranorol, alprenolol, oxprenolol, diltiazem and pinacidil; antitumors including 5-fluorouracil and tegafur; antibiotics including cefalexin, cefaclor and S-1108; antibacterials including cinoxacin, enoxacin and lomefloxacin, etc.

The thermomelting material (covering the first thermomelting material and the second thermomelting material) may be one which readily melts at an elevated temperature such as about 40° C. or higher, preferably from about 50° to 150° C., to give a melt having a low viscosity, preferably of such an extent as showing a self-flowability or self-fluidity. Typical examples of the thermomelting material are polyethylene glycols.

The thermomelting material may comprise a single hydrophilic or hydrophobic material or a mixture comprising at least one hydrophilic material and at least one hydrophobic material. The use of the mixture is sometimes recommendable to make the melting point lower. Also, the use of such mixture makes it possible to control the time for breaking or dissolving the coated composition, i.e. coated granules, as the final product in digestive organs.

Examples of the hydrophilic material are polyethylene glycols (PEG: macrogol) having an average molecular weight of not less than about 400, preferably of not less than about 1,000, more preferably from about 2,000 to 20,000, saccharides (e.g. D-glucose, maltose, fructose), sugar alcohols (e.g. D-mannitol, D-sorbitol), surfactants (e.g. sorbitan, Prulonic F68), etc. Among them, polyethylene glycols are usually preferred. Examples of the hydrophobic material are straight-chain saturated hydrocarbons (e.g. vaseline, paraffin), fats and oils (e.g. cacao butter, beef tallow, lard, hydrogenated soybeen oil, hydrogenated castor oil), animal and plant waxes (e.g. yellow beewax, white beewax), higher fatty acids (e.g. stearic acid), higher alcohols (e.g. cetanol, stearyl alcohol), hydrogenated plant oils (e.g. hydrogenated castor oil (Lubriwax 101), hydrogenated rapeseed oil (Lubriwax 103), polishing wax (a mixture of carnauba wax and paraffin), Presirol (a mixture of glycerol mono-, di- and tripalmitates)), etc.

One or more thermomelting materials appropriately chosen from hydrophilic and hydrophobic materials as above mentioned may be used as the binder (i.e. the first thermomelting material) at the granulating step and as the coating material (i.e. the second thermomelting material) at the coating step. In general, the second thermomelting material to be used as the coating material is preferred to have a lower melting point than that of the first thermomelting material to be used as the binder in order to prevent the softening or deformation of the granules as prepared in the granulating step. When, for instance, polyethylene glycol 6,000 is used as the binder at the granulating step, the use of polyethylene glycol 4,000 as the coating material at the coating step is favorable. Alternatively, a single thermomelting material may be used as the binder at the granulating step, and its mixture with any other thermomelting material(s) may be used as the coating material at the coating step, because a mixture of two or more thermomelting materials shows a lower melting point than that of each of them.

As the binder at the granulating step, the use of polyethylene glycol 6000 or hydrogenated castor oil is usually preferred. As the coating material at the coating step, the use of a mixture comprising a hydrophilic material and a hydrophobic material respectively in amounts of about 5 to 30 % by weight and about 10 to 60 % by weight is favorable.

If desired, the thermomelting material as the binder or the coating material may comprise any additive. When, for instance, such a thermomelting material which is apt to be auto-oxidized (e.g. polyethylene glycol, triglycerides) is used as the binder, an anti-oxidizing agent, particularly in an oily state at room temperature (e.g. alpha-dl-tocopherol, alpha-d-tocopherol, alpha-d-tocopherol acetate) may be incorporated therein in such a small amount as about 100 to 5,000 ppm, preferably about 500 to 2,000 ppm, for prevention of the auto-oxidation. Such addition of an anti-oxidizing agent sometimes produces a stabilization effect on the pharmaceutically active substance.

Further, for instance, additives as conventionally employed in solid pharmaceutical preparations may be incorporated into a thermomelting material as the coating material so as to control (i.e. promote or delay) disintegration or dissolution of the coated composition, i.e. coated granules, as the final product. Examples of such additives are saccharides (e.g. lactose), starchs (e.g. wheat starch, corn starch), inorganic materials (e.g. talc, calcium carbonate, titanium dioxide), etc.

Furthermore, for instance, conventional auxiliary agents such as pigments, flavors, stabilizers, preservatives and buffers may be used on preparation of the granules or the coated granules.

The binder may be used normally in such an amount as from about 0.05 to 0.4 part by weight to one part by weight of the pharmaceutically active substance. The coating material may be used usually in such an amount as from about 0.1 to 2 parts by weight to one part by weight of the granules. The coating layer to be formed on the granules is not necessarily required to be single and may have two or more layers. For instance, a single coating layer may be formed by the use of a coating material comprising a hydrophilic thermomelting material and a hydrophobic thermomelting material, or two coating layers may be formed by the use of a hydrophilic thermomelting material first and then by the use of a hydrophobic thermomelting material A typical example is the formation of a single coating layer or two coating layers by the use of about 0.05 to 0.3 part by weight, preferably about 0.08 to 0.2 part by weight, of a hydrophilic thermomelting material and about 0.1 to 0.6 part by weight, preferably about 0.2 to 0.4 part by weight of a hydrophobic thermomelting material based on 1 part by weight of the granules.

As stated above, the process of the invention comprises the steps of granulating and coating. Granulating is usually achieved by a centrifuged force granulating procedure, particularly a centrifuged force powder coating procedure. On the other hand, coating may be attained by various procedures such as a coating procedure using a pan or a coating procedure using a fluidized layer. As a typical example, granulating is carried out by rotating a mixture comprising the pharmaceutically active substance and a first thermomelting material as the binder under the condition that the first thermomelting material is kept in a melt state, and coating is carried out by rotating the resulting granules while application of a second thermomelting material as the coating material thereto under the condition that the second thermomelting material is kept in a melt state.

The steps of granulating and coating will be hereinafter explained more in detail.

The granulating step is normally effected by the use of a mixer (i.e. granulator) of rotary type or rolling type (e.g. universal mixer, high-speed mixer, super-mixer, centrifugal granulator) equipped with a heat control apparatus such as a jacket for circulating a heat-exchange fluid or a ventilator for heating and cooling. The container (i.e. a chamber wherein the starting materials are charged and granules are prepared) of the mixer is pre-heated to a temperature higher, preferably about 20°-40° C. higher, than the melting point of a first thermomelting material as the binder. Into the container thus pre-heated, a powdery premix of the pharmaceutically active substance and the first thermomelting material is charged, and rotation (preferably with agitation) is effected, whereby the first thermomelting material forms a melt and the particles of the pharmaceutically active substance cohere by the aid of the melt to give granules. Alternatively, the powdery premix may be charged into the container without its preheating, followed by heating to fuse the first thermomelting material and rotating to make the granules of the pharmaceutically active substance. Once the granulation begins, the granules are started to roll, and their particle size grows with application of the powdery premix thereto under rotation to give a desired particle size.

In order to enhance the efficiency of the granulation, nuclear or core particles such as microcrystalline cellulose (e.g. "Avicel" manufactured by Asahi Chemical) or granulated sugar may be introduced into the container of the mixer prior to the charge of the powdery premix. The container is heated while under rotation, and then the powdery premix is charged therein, whereby granulation starts. Rotation of the granules are continued with portionwise addition of the powdery premix thereto until the granules grow up to a desired particle size.

After the growth of the granules to a desired particle size, the temperature of the container is lowered to about 40° C. or less so that the grown granules are cooled to give hard and compact particles.

The above prepared granules, i.e. non-coated granules, are then subjected to coating to obtain coated granules. While the coating may be accomplished by various procedures, it is favorable to carry out such coating using a mixer of the same kind as employed in the granulating step. For the sake of convenience, the same mixer as actually used in the granulating step may be as such employed in the coating step.

Thus, the container of the mixer is pre-heated to keep at a temperature higher, usually about 20° C. higher, than the melting point of a second thermomelting material as a coating material. Into the container thus pre-heated, the non-coated granules as obtained in the granulating step are charged, and rotation is carried out. Under the continuation of rotation, the second thermomelting material or its mixture with any additive in a powdery state is portionwise added thereto, whereby a coating layer is formed on the surface of each particle. The thickness of the coating layer is appropriately controlled with the amount of the coating material, and as the result, the site or time for disintegration or dissolution of the coated granules as the final product can be properly regulated. In the above operation, the coating material comprising a second thermomelting material optionally with an additive may be charged first in the container without pre-heating and then subjected to heating under rotation until a coating layer having a desired thickness is formed on each particle. The formation of the coating layer may be effected in two or more stages using a coating material(s) of the same or different composition(s).

When the coating layer reaches a desired thickness, the temperature of the container is lowered, for instance, to about 40° C. or less for cooling under rotation so that coated granules having hard and compact coating layers at the surfaces are obtained.

When desired, any other appropriate operation may be applied between the granulating step and the coating step as above. For instance, the formation of a coating film comprising talc on the surfaces of the non-coated granules may be effected after the granulating step and before the coating step. Such talc film coating is effective in enhancing the physical strength of the non-coated granules so that those granules are protected from from breakage or disintegration during coating. It is also effective in taking up the pharmaceutically active substance in a powder form completely so that its attachment onto the surfaces of the granules in the coating step can be avoided. Incorporation of a suitable disintegrating agent into talc is sometimes advantageous, because the release of the pharmaceutically active substance from the resulting granules is delayed for a certain period of time. For the film formation, talc may be used in an amount of about 1 to 30 % by weight, preferably of about 5 to 20 % by weight based on the weight of the granules Practical embodiments of the invention are illustratively shown in the following Examples wherein % and part(s) are by weight unless otherwise indicated.

EXAMPLE 1 (Granulating)

Benexate hydrochloride/beta-cyclodextrin inclusion compound (i.e. TA 903) (40 parts), powdery polyethylene glycol 6000 (i.e. PEG 6000) having a particle size of 300 μm (48 mesh) or less (18 parts) and sugar powder (4 parts) were mixed together to make a uniform mixture. The mixture (150 g) was charged into an agitation type mixer ("Super-mixer" Type SM-5, manufactured by Kawata Seisakusho), and hot water was circulated through the jacket of the mixer, whereby the container of the mixer was heated to about 95° to 100° C. The agitation blade was started to rotate slowly, and when PEG 6000 was melted to wet the entire mixture, the rotation speed was raised to about 900 rpm so that the granulation started to give fine spherical particles. The spherical particles were rolled in the container, during which a mixture having the same composition as above (350 g) was portionwise added thereto so as to make the spherical particles grown. Water was introduced into the jacket of the mixer so that the container was cooled to a temperature below 40° C.

The thus obtained granules had the following size distribution:

| Particle size (μm) | Amount (g) |
| --- | --- |
| more than 710 (24 mesh on) | 22.2 (4.5%) |
| 710–420 (24–35 mesh) | 149.7 (30.4%) |
| 420–150 (35–100 mesh) | 302.0 (61.4%) |
| less than 150 (100 mesh pass) | 18.1 (3.7%) |
| Total | 492.0 |

EXAMPLE 2 (Granulating)

Granules having a particle size of 150 to 420 um (35 to 100 mesh) (150 g) as obtained in Example 1 were charged in the container of a mixer, and the agitation blade was rotated slowly. The temperature of the container was elevated to about 95° to 100° C. while slow rolling of the granules. When the surfaces of the granules began to melt, the rotation speed was raised, and a mixture having the same composition as used in Example 1 (350 g) was portionwise added thereto so as to make the spherical particles grown. Water was introduced into the jacket of the mixer so that the container was cooled to a temperature below 40° C.

The thus obtained granules had the following size distribution:

| Particle size (μm) | Amount (g) |
| --- | --- |
| more than 710 (24 mesh on) | 14.6 (3.0%) |
| 710–420 (24–35 mesh) | 323.3 (65.5%) |
| 420–150 (35–100 mesh) | 103.9 (21.1%) |
| less than 150 (100 mesh pass) | 51.5 (10.4%) |
| Total | 493.3 |

EXAMPLE 3 (Coating)

Stearyl alcohol (6 parts) and polyethylene glycol (i.e. PEG 4000) (4 parts) were mixed together, and the resultant mixture was heated at 80° C. for fusion, followed by agitation. After cooling, the solidified product was crushed and pulverized to make a premix having a particle size of 300 μm or less as a coating material. Using the premix, the following two coating compositions were prepared:

| | Part(s) |
| --- | --- |
| First coating composition: | |
| Talc | 2 |
| Corn starch | 2 |
| Premix | 1 |
| Total | 5 |
| Second coating composition: | |
| Talc | 2 |
| Lubriwax | 2 |
| Premix | 1 |
| Total | 5 |

The granules having a particle size of 420 to 710 μm (24 to 35 mesh) (250 g) as prepared in Example 1 or 2 were charged into the container of a mixer ("Super-mixer" Type SM-5) and rotated slowly under agitation, whereby the granules were rolled. Hot water was circulated in the jacket of the mixer, and the temperature of the container was elevated to about 60° C. Then, the rotation speed was raised, and the first coating composition (150 g) was portionwise added thereto so as to coat the granules. Then, water was introduced into the jacket of the mixer to lower the temperature of the container below 40° C.

The coated granules thus obtained had a particle size of 420 to 1,000 μm (16 to 35 mesh) and a total weight of 402.5 g. The coating rate as calculated according to the following formula was 61 %:

$$\frac{\text{Weight of granules after coating} - \text{Weight of granules before coating}}{\text{Weight of granules before coating}} \times 100$$

Hot water was again introduced into the jacket so as to elevate the temperature of the container to about 57° C. The above obtained coated granules (402 g) were charged into the container, and rotation with agitation was carried out, during which the second coating composition was portionwise added thereto to coat the surfaces of the coated granules. Water was introduced into the jacket so as to lower the temperature of the container below 40° C.

The coated granules thus obtained had a particle size of 420 to 1,000 μm (16 to 35 mesh) and a total weight of 482 g. The coating rate as calculated according to the following formula was 20 %:

$$\frac{\text{Weight of the second coated granules} - \text{Weight of the first coated granules}}{\text{Weight of the first coated granules}} \times 100$$

The premix as prepared in Example 3 (1 part) was mixed together with talc (2 parts), corn starch (1.2 parts) and Lubriwax 101 (0.8 part) to give a powdery mixture for delayed release coating. The granules having a particle size of 420 to 710 μm (24 to 35 mesh) (250 g) as prepared in Example 1 or 2 were charged into the container of a mixer ("Super-mixer" Type SM-5), and slow rotation with agitation was carried out, during which hot water was circulated through the jacket of the mixer to heat the container at a temperature of about 58° C. The rotation speed was raised, and the powdery mixture was portionwise added thereto to make a coating layer at the surfaces of the granules. Then, water was introduced into the jacket to lower the temperature of the container below 40° C., and the coated granules were cooled.

The coated granules thus obtained had a particle size of 420 to 1,000 μm (16 to 35 mesh) and a total weight of 510 g. The coating rate as calculated according to the formula given in Example 3 was 104 %.

EXAMPLE 5 (Granulating with cores)

TA 903 pulverized to a particle size of 150 μm or less (100 mesh pass) (20 parts), PEG 6,000 (9 parts) and sugar powder (2 parts) were mixed uniformly to make a premix for granulation. Granular sugar having a particle size of 210 to 300 μm (48 to 65 mesh) (150 g) as nuclear or core particles was charged in the container of a mixer ("Super-mixer" Type SM-5) and slowly rotated with agitation while heating to about 95° C. or more by circulating hot water through the jacket. After the nuclear or core particles were heated, the rotation speed was raised to about 900 rpm, and the premix (400 g) was portionwise added thereto. Water was introduced into the jacket, and the container was cooled to a temperature below 40° C.

The thus obtained granules had the following size distribution:

| Particle size (μm) | Amount (g) |
| --- | --- |
| more than 840 (20 mesh on) | 56.1 (10.3%) |
| 840-500 (20-32 mesh) | 76.0 (14.0%) |
| 500-300 (32-48 mesh) | 333.0 (61.2%) |
| 300-210 (48-65 mesh) | 70.0 (12.9%) |
| less than 200 (65 mesh pass) | 9.1 (1.6%) |
| Total | 544.2 |

EXAMPLE 6 (Granulating with cores)

PEG 6000 having a particle size of about 180 μm or less (80 mesh pass) was admixed with alpha-d-tocopherol (i.e. VE) in an amount of 900 ppm to make a uniform mixture (i.e. VE-added PEG 6000). VE-added PEG 6000 (15 kg) and TA 903 powder (40 kg) were mixed together and passed through a screen (80 mesh) to make a premix for granulation. Separately, talc (9.5 kg) was admixed with VE-added PEG 6000 (250 g) and microcrystalline cellulose (1.25 kg) as a disintegrating agent to make a mixed powder for talc film formation.

Into the container of a centrifugal rotary granulator ("CF-1000" manufactured by Freund Industry) provided with a regulator for heating temperature, the wall temperature of said container having been adjusted to about 106° C., microcrystalline cellulose powder ("Avicel") having a 50% average particle size of 350 μm (27.57 kg) as nuclear or core particles was charged, and rotation was carried out at 100 rpm. When the core or nuclear particles were heated to about 95° C., the above prepared premix for granulation was portionwise applied thereto with a supply speed of 0.5 kg/min. With the progress of the fusion of PEG 6000 in the premix, the nuclear or core particles were wetted, and the amount of TA 903 powder attaching to the nuclear or core particles was increased. The supply speed of the premix was gradually increased until the attaching rate of TA 903 powder was made constant, and then the remaining amount of the premix was applied thereto with a supply speed of 3 kg/min to make hard and compact spherical granules. In comparison with the weight of the nuclear or core particles, the weight increase was 199.5%.

Onto the spherical granules thus obtained, an entire amount of the above prepared mixed powder for talc coating was applied at a supply speed of 3 kg/min, followed by cooling to about 70° C. to make a talc coating film at the surfaces of the spherical granules. In comparison with the weight of the spherical granules, the weight increase was 13.3%.

The thus obtained granules having a talc coating film on the surfaces had an average particle size of about 600 μm and an average particle weight of about 938 (containing about 400 mg of TA 903). Their particle size distribution was as follows:

| Particle size (μm) | Amount (kg) |
| --- | --- |
| more than 840 (24 mesh on) | 4.10 (4.3%) |
| 840-355 (20-42 mesh) | 87.38 (93.2%) |
| less than 355 (42 mesh pass) | 0.16 (0.2%) |
| Total | 91.64 |

Of the granules having a talc coating film on the surfaces as above prepared, those having an average particle size of 355 to 840 μm (20 to 42 mesh) were collected and subjected to coating in Example 7.

EXAMPLE 7 (Coating)

PEG 4000 having a particle size of about 180 μm or less (80 mesh pass) was admixed with VE in an amount of 900 ppm to make a uniform mixture (i.e. VE-added PEG 4000). VE-added PEG 4000 (3.94 kg), stearyl alcohol powder having a particle size of about 180 μm or less (80 mesh pass) (2.64 kg), corn starch (2.64 kg), hydrogenated castor oil (7.88 kg) and talc (13.93 kg) were mixed together to make a mixed powder for coating.

Into the container of the granulator as used in Example 6, said container having been pre-heated to about 65° C., the granules having a talc coating film on the surfaces (355 to 840 μm) (50.00 kg) as prepared in Example 6 were charged, and rotation was carried out at 100 rpm. When the temperature of the granules reached to a temperature of about 62° C., the mixed powder for coating as above prepared was portionwise applied thereto with a supply speed of 0.2 kg/min. With the progress of the fusion of PEG 4000 in the mixed powder, the granules were wetted, and the amount of the mixed powder attaching to the surfaces of the granules was increased. The supply speed of the mixed powder was gradually increased until the attaching rate of the mixed powder was made constant, and then the remaining amount of the mixed powder was applied thereto with a supply speed of 3 kg/min, followed by cooling the temperature below 50° C. to make hard and compact coated granules. In comparison with the weight of the granules, the weight increase was 56.8%.

The thus obtained coated particles had an average particle size of about 700 μm and an average particle weight 1541 mg (containing 400 mg of TA 903). Their particle size distribution was as follows:

| Particle size (μm) | Amount (kg) |
| --- | --- |
| more than 1000 (16 mesh on) | 0.37 (0.4%) |
| 1000–355 (16–42 mesh) | 83.03 (98.7%) |
| less than 355 (42 mesh pass) | 0.51 (0.6%) |
| Total | 83.91 |

TEST EXAMPLE 1

With the coated granules having two coating layers at the surfaces (particle size, 420 to 1000 μm (16–35 mesh)) as obtained in Example 3, the dissolution test was carried out according to the puddle method as described in Japanese Pharmacopoeia XI. As the dissolution media, there were used the 1st test solution (prepared by adding water to a mixture of sodium chloride (2.0 g) and dilute hydrochloric acid (24.0 ml) to make a total volume of 1,000 ml; pH, about 1.2) (900ml) and purified water (900 ml). Measurement was made on TA 903 under a rotation speed of 100 rpm.

The results (dissolution curve) are shown in FIG. 1 of the accompanying drawings, from which it is understood that the dissolution of TA 903 is delayed about 5 minutes. In fact, the release of TA 903 from the coated granules as above in the mouth was prevented for several minutes, and therefore no bitter taste was produced on the oral administration.

TEST EXAMPLE 2

With the coated granules (particle size, 420 to 1000 μm (16–35 mesh)) as obtained in Example 4, the dissolution test was carried out according to the puddle method as described in Japanese Pharmacopoeia XI. As the dissolution media, there were used the 1st test solution (900 ml) and purified water (900 ml). Measurement was made on TA 903 under a rotation speed of 100 rpm.

Figure 2:
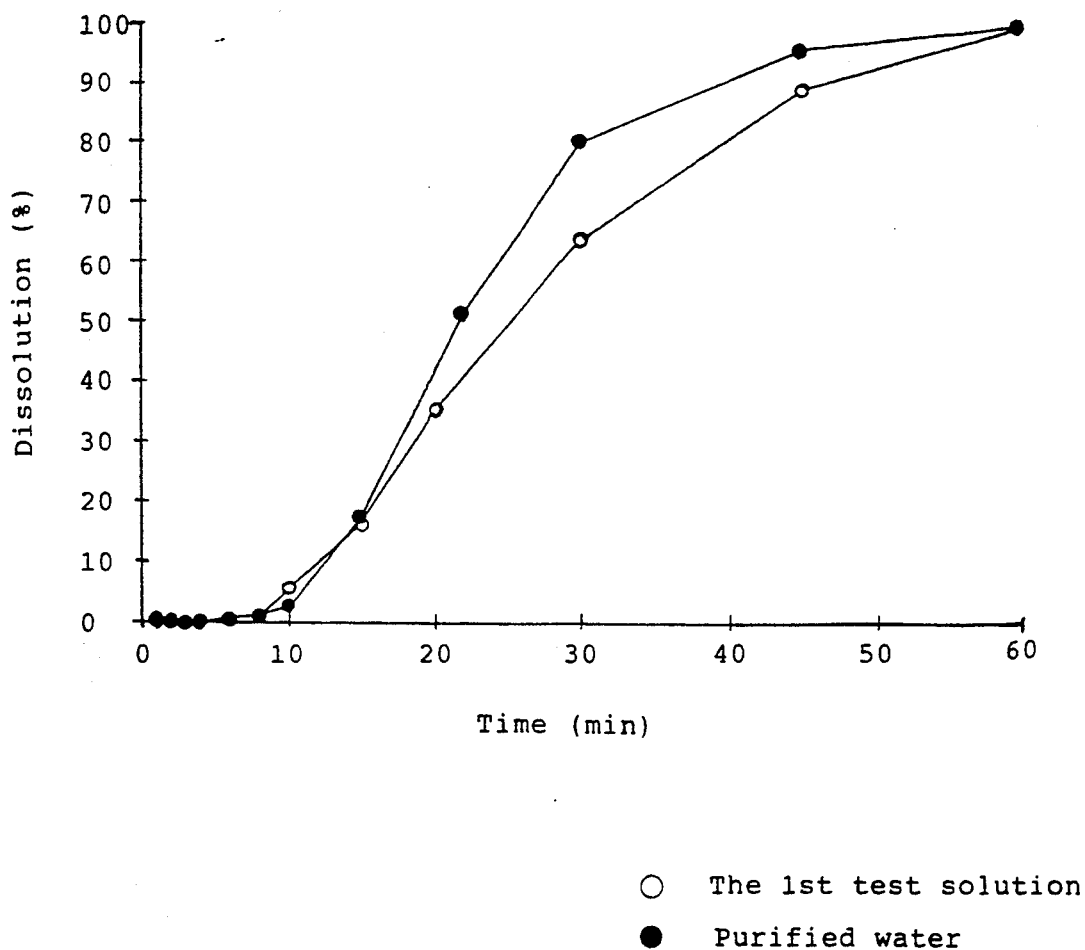

The results (dissolution curve) are shown in FIG. 2 of the accompanying drawings, from which it is understood that the dissolution of TA 903 is delayed about 5 minutes, and then performed gradually. Such dissolution curve indicates the characteristics of the coated granules of a release controlled type.

TEST EXAMPLE 3

With the coated granules (average particle size, about 700 μm) as obtained in Example 7, the dissolution test was carried out according to the puddle method as described in Japanese Pharmacopoeia XI. As the dissolution media, there were used the 1st test solution (900 ml), the 2nd test solution (prepared by adding water to a mixture of 0.2 M potassium dihydrogen phosphate solution (250 ml) and 0.2 N sodium hydroxide solution (118 ml) to make a total volume of 1,000 ml; pH, about 6.8) (900 ml) and purified water (900 ml). Measurement was made on TA 903 under a rotation speed of 100 rpm.

Figure 3:
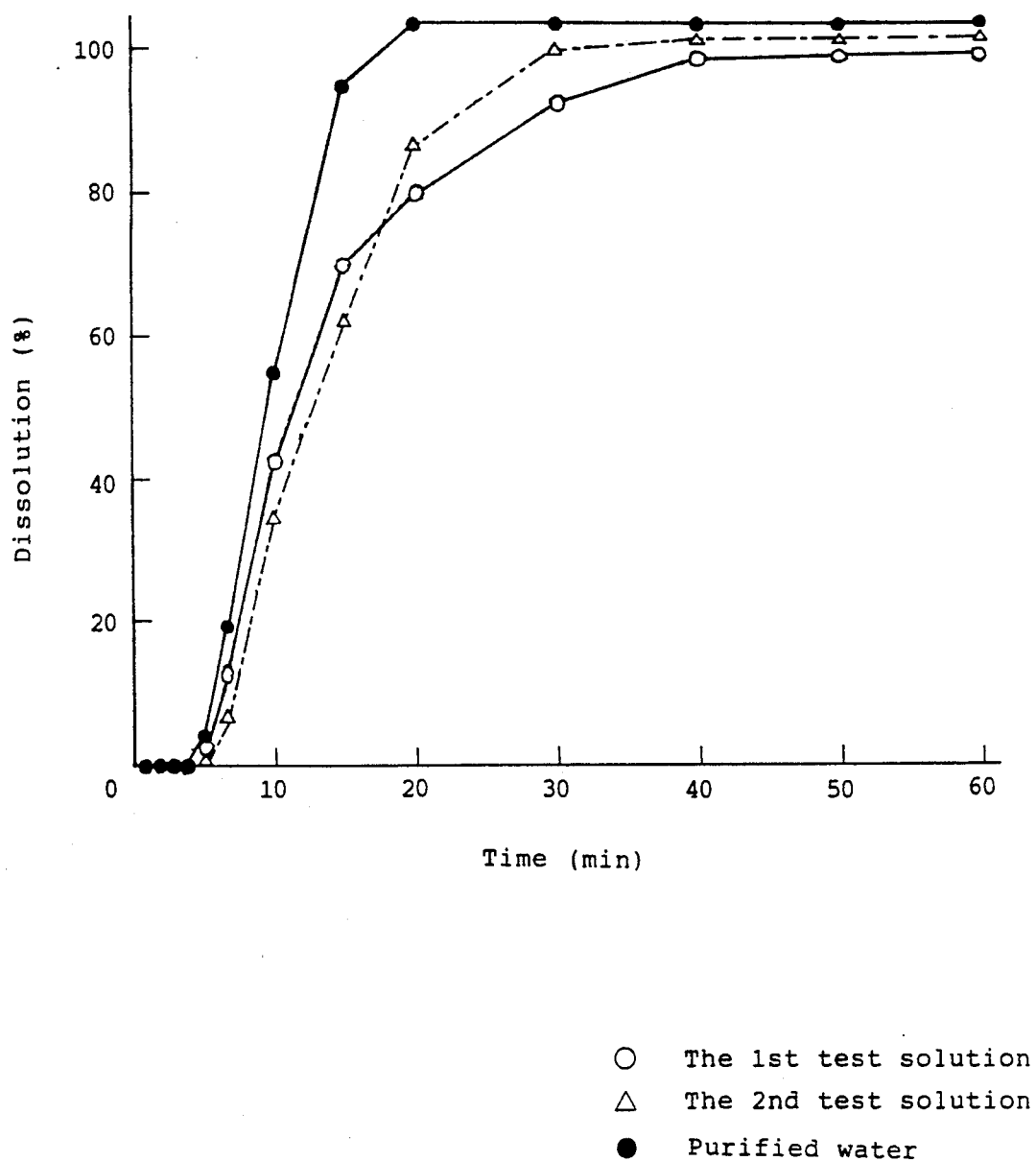

The results (dissolution curve) are shown in FIG. 3 of the accompanying drawings, from which it is understood that the dissolution of TA 903 is delayed about 5 minutes.

What is claimed is:

1. Orally administrable coated granules of a pharmaceutically active substance stable to heat and sensitive to a solvent, which granules do not substantially release said pharmaceutically active substance during their stay in an oral cavity and, after passing through the oral cavity, dissolve or disintegrate quickly to release said pharmaceutically active substance and each granule being in a discrete form and comprising fine particles of said pharmaceutically active substance bound to each other by a first thermomelting polyethylene glycol material melting at a temperature of about 50° to 150° C. as a binder in an amount of from about 0.05 to 0.4 parts by weight to one part by weight of said pharmaceutically active substance and coated with a second thermomelting material which is a mixture of polyethylene glycol and a hydrophobic thermomelting material in a ratio of 1:2 by weight, said mixture having a melting point of about 50° to 150° C. but which is lower than the melting point of the first thermomelting polyethylene glycol material in an amount of from about 0.1 to 2 parts by weight to one part by weight of said granule, the coated granules being prepared from a mixture comprising fine particles of said pharmaceutically active substance and said first polyethylene glycol thermomelting material by a centrifuged force granulation procedure without using any solvent to form non-coated granules and subsequently coated the non-coated granules with said second thermomelting material by a centrifuged force coating procedure without using any solvent.

2. Orally administrable coated granules of a pharmaceutically active substance stable to heat and sensitive to a solvent, which granules do not substantially release said pharmaceutically active substance for at least 5 minutes after the oral administration and then, after passage through the oral cavity, dissolve or disintegrate within about one hour to release said pharmaceutically active substance and each granule being in a discrete form a comprising fine particles of said pharmaceutically active substance bound to each other by a first thermomelting polyethylene glycol material having a melting point of about 50° to 150° C. as a binder in an amount of from about 0.05 to 0.4 parts by weight to one part by weight of said pharmaceutically active substance and coated with a second thermomelting material which is a mixture of polyethylene glycol and a hydrophobic thermomelting material in a ratio of 1:2 by weight, said mixture having a melting point of about 50° to 150° C. but which is lower than the melting point of the first thermomelting polyethylene glycol material in an amount of from about 0.1 to 2 parts by weight to one part by weight of said granule, the coated granules being prepared from a mixture comprising fine particles of said pharmaceutically active substance and said first thermomelting polyethylene glycol material by a centrifuged force granules with said second thermomelting material by a centrifuged force coating procedure without using any solvent.

3. Orally administrable coated granules according to claim 1 wherein the pharmaceutically active substance is a cyclodextrin inclusion compound of 4-guanidinomethylcyclohexanecarboxylic acid 1'-benzyloxycarbonylphenyl ester hydrochloride.

4. Orally administrable coated granules according to claim 2 wherein the pharmaceutically active substance is a cyclodextrin inclusion compound of 4-guanidinomethylcyclohexanecarboxylic acid 1'-benzyloxycarbonylphenyl ester hydrochloride.

5. Orally administrable coated granules according to claim 1 wherein the first thermomelting polyethylene glycol material has an average molecular weight of not less than about 1000.

6. Orally administrable coated granules according to claim 2 wherein the first thermomelting polyethylene glycol material has an average molecular weight of not less than about 1000.

7. Orally administrable coated granules according to claim 1 wherein the first thermomelting polyethylene glycol material comprises additionally a small amount of alpha-d-tocopherol.

8. Orally administrable coated granules according to claim 2 wherein the first thermomelting polyethylene glycol material comprises additionally a small amount of alpha-d-tocopherol.

* * * * *